United States Patent [19]

Eckenhoff et al.

[11] Patent Number: 4,684,524
[45] Date of Patent: * Aug. 4, 1987

[54] RATE CONTROLLED DISPENSER FOR ADMINISTERING BENEFICIAL AGENT

[75] Inventors: James B. Eckenhoff, Los Altos; Richard Cortese, Los Gatos; Felix A. Landrau, Milpitas, all of Calif.

[73] Assignee: ALZA Corporation, Palo Alto, Calif.

[*] Notice: The portion of the term of this patent subsequent to Jun. 17, 2003 has been disclaimed.

[21] Appl. No.: 763,493

[22] Filed: Aug. 8, 1985

Related U.S. Application Data

[63] Continuation-in-part of Ser. No. 590,778, Mar. 19, 1984, Pat. No. 4,595,583.

[51] Int. Cl.$^4$ .................. A61K 9/22; A61M 31/00
[52] U.S. Cl. ......................... 424/469; 514/30; 514/53; 604/890; 604/892
[58] Field of Search ............. 424/15, 19, 469; 604/890, 892; 514/30, 53

[56] References Cited

U.S. PATENT DOCUMENTS

| | | | |
|---|---|---|---|
| 2,340,037 | 1/1944 | Zipper | 167/83 |
| 3,732,865 | 5/1973 | Higuchi et al. | 128/260 |
| 3,760,804 | 9/1973 | Higuchi et al. | 128/260 |
| 3,769,895 | 9/1973 | Higuchi | 128/260 |
| 3,845,770 | 11/1974 | Theeuwes et al. | 128/260 |
| 3,929,132 | 12/1975 | Higuchi | 128/260 |
| 3,995,632 | 12/1976 | Nakano et al. | 128/260 |
| 4,034,756 | 7/1976 | Higuchi et al. | 128/260 |
| 4,088,864 | 5/1978 | Theeuwes et al. | 219/121 |
| 4,178,361 | 12/1979 | Cohen et al. | 424/22 |
| 4,196,187 | 4/1980 | Dannelly et al. | 424/21 |
| 4,199,569 | 4/1980 | Chabala et al. | 536/7.1 |
| 4,200,098 | 4/1980 | Ayer et al. | 128/260 |
| 4,235,236 | 11/1980 | Theeuwes | 128/260 |
| 4,285,987 | 8/1981 | Ayer et al. | 427/3 |
| 4,351,825 | 9/1982 | Sothmann | 424/22 |
| 4,389,397 | 6/1983 | Lo et al. | 514/53 |
| 4,595,583 | 6/1986 | Eckenhoff et al. | 424/15 |

FOREIGN PATENT DOCUMENTS

| | | |
|---|---|---|
| 19250 | 3/1972 | Australia . |
| 2729068 | 11/1979 | Fed. Rep. of Germany . |
| 1540258 | 9/1968 | France . |

Primary Examiner—Ronald W. Griffin
Attorney, Agent, or Firm—Paul L. Sabatine; Edward L. Mandell; Steven F. Stone

[57] ABSTRACT

A dispenser is disclosed for delivering a beneficial agent. The dispenser comprises (1) a housing defining an internal space, (2) a heat-responsive composition containing a beneficial agent in the space, (3) an osmotically effective solute in the space, and (4) at least one passageway in the housing for delivering the beneficial agent from the dispenser.

40 Claims, 7 Drawing Figures

4,684,524

RATE CONTROLLED DISPENSER FOR ADMINISTERING BENEFICIAL AGENT

CROSS-REFERENCE TO RELATED APPLICATION

This patent application is a continuation-in-part of patent application U.S. Ser. No. 06/590,778 filed on Mar. 19, 1984, now U.S. Pat. No. 4,595,583, issued June 17, 1986.

FIELD OF THE INVENTION

The present invention relates to a new and useful dispenser for the rate controlled administration of a beneficial agent to an agent receptor. More particularly, the invention relates to a dispenser comprising a wall that surrounds an internal lumen containing a thermo-responsive beneficial agent formulation and a fluid displacement member. The invention concerns also laminates useful for manufacturing the dispenser.

BACKGROUND OF THE INVENTION

There long has been a need in the medical and veterinary dispensing arts for a dispenser that is capable of administering a beneficial agent at a relatively controlled rate over a prolonged period of time. For example, the need exists for increasing the maximum time of therapeutic effectiveness of medicinals whose maximum time of therapeutic effectiveness, when administered in conventional dosage form such as a tablet, is only a few hours. The patient or veterinary animal using such a conventional form must be administered repeated dosages at frequent intervals. Moreover, during intervals between dosages the therapeutic level in the blood decreases due to metabolic activities and the level can become so low that it is practically ineffective. Thus, as a result of frequent doses, the level of medicine available for therapy will fluctuate between doses. The need for a dispenser exists also that can deliver a beneficial agent that is difficult to deliver, usually attributable to some physical property. For example, beneficial agent that are insoluble in aqueous fluids are difficult to deliver because they do not form an aqueous solution and, accordingly, they cannot be dispensed in solution form from prior art dispensing devices. Also, many beneficial agents exhibit lipid solubilities and these beneficial agents are difficult to deliver by conventional dosage forms.

OBJECTS OF THE INVENTION

It is a principle object of this invention to provide both a novel and useful dispenser for dispensing a beneficial agent and which dispenser fulfills the pressing need known to the prior art.

It is another object of this invention to provide a dispenser that can deliver a beneficial agent at a controlled rate over a prolonged period of time thereby overcoming the shortcomings associated with the prior art dosage forms.

It is another object of this invention to provide a dispenser that is self-contained, self-starting and self-powered in a fluid environment of use for dispensing a beneficial agent that is difficult to deliver over time.

It is another object of the invention to provide a dispenser device comprising a wall that surrounds a lumen comprising a thermo-responsive sensitive means containing a beneficial agent and a volume displacement driving means for delivering the beneficial agent from the dispenser.

It is another object of this invention to provide a dispenser comprising (1) a wall comprising in at least a part a composition permeable to fluid which wall surrounds, (2) an internal lumen housing, (3) a thermo-responsive composition containing a beneficial agent, and (4) an agent displacing means, and which dispenser administers the beneficial agent by the combined physical-chemical operations of the thermo-responsive composition melting or softening, and becoming fluid to semisolid or the like, and the agent displacement means consuming fluid and occupying space in the area initially occupied by the thermo-responsive composition, thereby displacing the composition from its initial area and urging it through (5) means in the wall for dispensing the beneficial agent.

It is another object of this invention to provide a dispenser that can deliver a beneficial drug contained in a thermo-responsive, lipophilic pharmaceutical acceptable carrier that softens in the presence of thermal energy absorbed from the environment of use and forms a dispensable composition that is innocuous, and can be dispensed from the dispenser over time.

It is another object of this invention to provide a dispenser containing a thermo-responsive eutetic composition comprising at least two components and at least one drug, which eutetic composition has a melting point approximately the same as the temperature of a warm-blooded animal recipient, and is dispensed from the dispenser at said temperature.

It is another object of this invention to provide a dispensing system manufactured as a dispenser comprising an inner positioned capsule housing a thermo-responsive lipophilic or a thermo-responsive hydrophobic, or a thermo-responsive hydrophilic composition comprising from insoluble to soluble drugs, and which thermo-responsive composition in response to energy input present in a biological environment of use, changes its form and becomes dispensable for operative delivery from the dispensing system.

It is another object of this invention to provide a dispenser for dispensing a beneficial drug to an animal, which dispenser contains a thermo-responsive composition and a fluid utilizing component, and which composition comprises a beneficial agent that is insoluble in an aqueous environment and can be housed in the dispenser in a non-aqueous dispensing carrier that can be delivered to an animal.

It is another object of this invention to provide a dispensing device designed as a dispenser useful for delivering a beneficial agent to an animal.

Other objects, features and advantages of the invention will be more apparent to those skilled in the dispensing art from the following detailed description of the specification, taken in conjunction with the drawing figures and the accompanying claims.

BRIEF DESCRIPTION OF THE DRAWINGS

In the drawing figures, which are not drawn to scale, but are set forth to illustrate various embodiments of the invention, the drawing figures are as follows.

In the drawing figures and in the specification, like parts in related figures are identified by like parts. The terms appearing earlier in the specification and in the description figures, as well as embodiments thereof, are further detailed elsewhere in the disclosure.

DETAILED DESCRIPTION OF THE DRAWINGS

Figure 1:
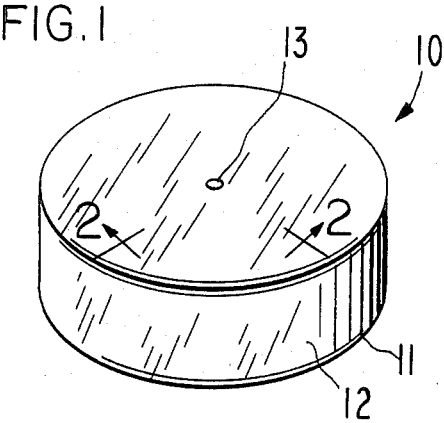
FIG. 1 is a partial view of a dispenser designed for orally administering a beneficial agent in the gastrointestinal tract of a warmblooded animal.

Turning now to the drawing figures in detail, which are examples of various delivery devices provided by the invention and which examples ARC 1350 are not to be construed as limiting, one example of a dispenser is seen in FIG. 1. In FIG. 1 dispenser 10 is seen comprising a body member 11 having a wall 12 that surrounds and forms a compartment, not seen in FIG. 1. Dispenser 10 is provided with a means 13 in wall 12 for releasing a beneficial agent from dispenser 10 to the environment of use over time.

Figure 2:
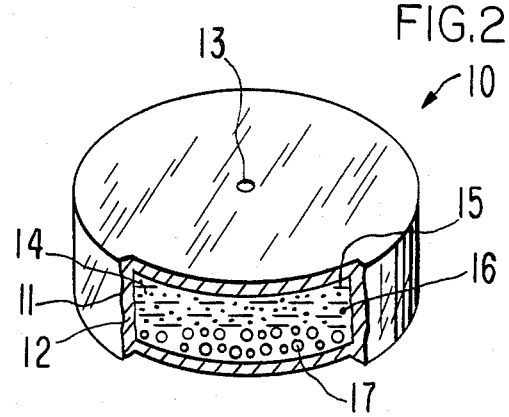
FIG. 2 is an opened view of FIG. 1 through 2—2 thereof for illustrating the internal structure of the dispenser of FIG. 1.

In FIG. 2, a dispenser 10 is seen on open section along 2—2 of FIG. 1. In FIG. 2, dispenser 10 comprises body 11, wall means 12, that surround and form an internal compartment 14, and agent releasing means 13 for connecting internal compartment 14 with the exterior of dispenser 10. Wall 12 of dispenser 10 is sectioned for depicting internal compartment 14. Wall 12 is formed of a non-toxic composition that, in a presently preferred embodiment, maintains its physical and chemical integrity during the delivery period; that is, wall 12 does not erode or lose its structural integrity during the agent dispensing period. Wall 12, in one presently preferred embodiment, comprises in at least a part a permeable wall forming composition that is substantially permeable to the passage of an external fluid. Wall 12, in another presently preferred embodiment, is formed in at least a part of a semipermeable composition that is permeable in at least a part to the passage of fluid and it is substantially impermeable to the passage of a beneficial agent and other ingredients present in delivery system 10. In another embodiment, wall 12 comprises in at least a part of a permeable or a semipermeable composition with the remainder of wall 12 comprising a wall composition impermeable to the passage of fluid, or the remainder of wall 12 comprising a polymeric composition that is a means 13 for releasing a beneficial agent from dispenser 10.

Internal compartment 14 contains a thermo-responsive composition 15, identified by dashes. Thermo-responsive composition 15 is a heat-sensitive, thermo-absorbing composition that uses thermal energy for changing its viscosity from a storage state to a dispensable state in situ. Thermo-responsive composition 15 contains a beneficial agent 16, identified by dots, homogeneously or heterogeneously dissolved, or dispersed, or blended therein. Internal compartment 14 contains also means 17 for delivering thermo-responsive beneficial agent composition 15 from dispenser 10. Means 17, identified by circles, is in layered contact with a contacting surface formed by the interface of thermo-responsive composition 15 and delivery means 17. Means 17 comprises at least one osmotically effective composition that, in a preferred embodiment, is initially present in a substantially-dry state. The osmotically effective compound absorbs and/or imbibes fluid that passes through wall 12 and continuously forms a solution in situ in compartment 14. The solution occupies space in compartment 14 and it displaces thermo-responsive beneficial agent composition 15 that is continuously forming a dispensable composition from its initial space. This continual displacement applies a driving force against thermo-responsive composition 16 thereby urging it through releasing means 13 from dispenser 10. Means 13 extends through wall 12 for connecting compartment 14 with the exterior of dispenser 10. In FIGS. 1 and 2, releasing means 13, in one embodiment, is a passageway for delivering thermo-responsive beneficial agent composition 15 from dispenser 10 to a fluid, heat-producing environment of use.

Figure 3:
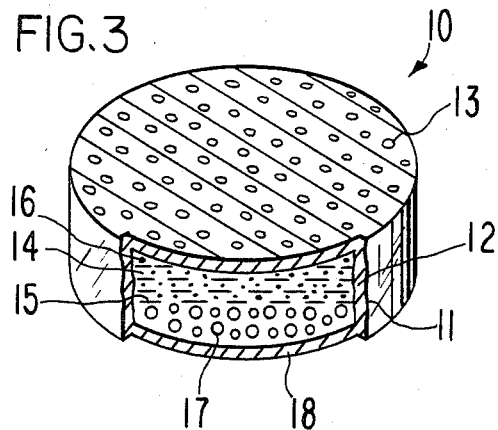
FIG. 3 is an opened view of a dispenser provided by the invention, which dispenser is designed with means for forming a releasing passageway in operation in a fluid environment of use.

FIG. 3 depicts another embodiment of dispenser 10 provided by the invention. FIG. 3 is an opened view of dispenser 10. In FIG. 3, dispenser 10 comprises body 11, wall 12, internal compartment 14, thermo-responsive composition 15 containing beneficial agent formulation 16 and osmotically effective solution producing means 17. In FIG. 3, dispenser 10 wall 12 comprises a releasing means 13 formed of a microporous composition. In this embodiment, a section of wall 12 contains a pore forming agent that is removed from wall 12 in the environment of use to form a pore of controlled release dimensions, or in another embodiment wall 12 is formed in a part of a microporous composition comprising a plurality of micropores of precontrolled dimensions. In FIG. 3, wall 12 comprises also in at least a part a section 18 formed of a composition permeable to the passage of fluid and substantially impermeable to the passage of osmotically effective compound 17. In FIG. 3, thermo-responsive composition 15 containing beneficial agent formulation 16 is immediately adjacent to the interior surface of microporous releasing means 13 for its passage through the pores. The microporous beneficial agent releasing surface is an additional dispensing advantage provided by the invention, as it functions like a diffuser for diffusing the agent over a larger agent receiving surface. This action of presenting the agent over a broad tissue area lessens the incidence of tissue irritation associated with tissue irritating agents.

Figure 4:
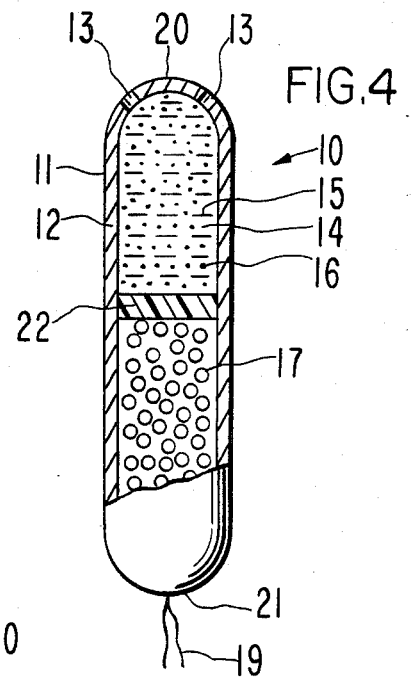
FIG. 4 is a view of a dispensing device provided by the invention, with its wall broken open, which dispensing device is designed for delivering a beneficial agent into a body passageway such as the anorectal and vaginal passageways.

FIG. 4 depicts another embodiment of dispenser 10 provided by the invention. FIG. 4 depicts dispenser 10 designed for easy placement in a body passageway, such as a vagina, or the ano-rectal passageway or, optionally, for easy placement in a muscle tissue for use as an implant. Dispenser 10 has an elongated, cylindrical self-sustaining shape, and it comprises a rounded lead end 20 and a trailing end 21 suitably equipped with a manually controlled string 19 for easily removing dispensing device 10 from a body passageway. FIG. 4 is an opened view of dispenser 10. Dispenser 10 comprises wall 12 that surrounds and defines internal space 14. Internal space 14 comprises a thermo-responsive composition 15 containing beneficial agent formulation 16 and a fluid sensitive osmotically effective compound 17, for example an aqueous or a biological fluid, that is a means for producing a fluid environment in space 14. Dispenser 10, in the embodiment depicted, comprises a first and a second passageway means 13 for releasing thermixotropic beneficial agent composition from dispenser 10. Dispenser 10 comprises an optional layer 22 of a polymeric composition that (a] substantially prevents intermingling of thermo-responsive composition 15 and an aqueous-like osmotic solute solution 17, or (b) is a means for transmitting the force generated by forming an osmotic solute solution against thermo-responsive composition 15 for enhancing its delivery through a pair of delivery means 13.

Figure 5:
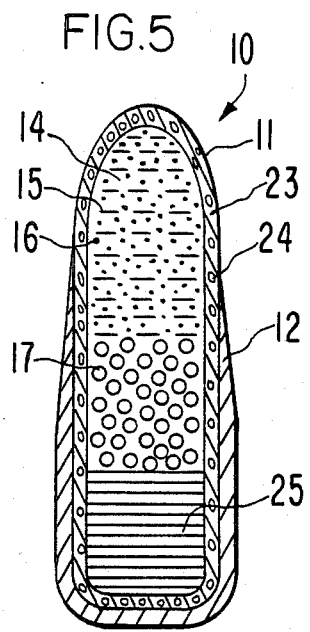
FIG. 5 is an opened view of a dispensing device, a dispenser, illustrating the internal structure of the dispenser comprising an inside wall coated in part by an outside wall thereby defining a lumen containing a heat sensitive composition, a composition for absorbing and imbibing fluid, and a density member.

FIG. 5 depicts another dispenser 10 provided by the invention. FIG. 5 depicts dispenser 10 in opened section, which dispenser 10 is adapted, shaped and sized for orally admitting into the rumen of a ruminant. In FIG. 5, dispenser 10 comprises an internal wall 23 formed of a microporous polymeric composition wall 23 which, in one embodiment, contains a pore forming agent that is dissolved or leached from wall 23 to form a releasing pore 24 of controlled dimensions. In another embodiment wall 23 can be a microporous polymeric composition that comprises preformed agent releasing pores 24. In either manufacture the pores 24 are a means for dispensing beneficial agent 16 from dispenser 10. Dispenser 10 comprises further an exterior wall 12 comprising in at least a part a permeable composition or in at least a part a semipermeable composition permeable to the passage of fluid and, in the latter embodiment, substantially impermeable to the passage of beneficial agent. The laminated wall surrounds internal compartment 14 containing thermo-responsive composition 15 having beneficial agent 16 dispersed therein, solution producing osmotic solute composition 17 and a density member 25. Density member 25, a densifier, is a component of dispenser 10 for keeping dispenser 10 in the rumen of an animal during the beneficial agent dispensing period.

Figure 6:
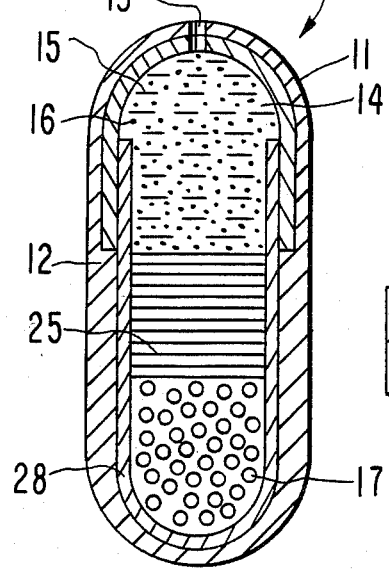
FIG. 6 is an opened view of a dispensing system designed as a dispenser, which dispenser comprises an inside wall and an outside wall surrounding an internal space for containing a beneficial agent and means for urging same from the dispenser at a controlled rate to an animal over a prolonged period of time; and, FIG. 7 depicts a laminate useful for manufacturing a dispenser provided by the invention.

FIG. 6 illustrates another embodiment of a delivery dispenser 10 provided by the invention. FIG. 6 is an opened view of therapeutic dispenser 10. Dispenser 10 of FIG. 6 comprises body 11, external wall 12 and a passageway 13. Wall 12 surrounds an internal capsule 26. Wall 12, in one presently preferred embodiment, comprises a wall that permits the passage of fluid, or a semipermeable wall forming composition that is permeable to the passage of an external fluid present in the environment of use, and it is substantially impermeable to the passage of a beneficial agent and other ingredients in compartment 14. In another embodiment, semipermeable wall 12 can partly surround internal capsule 25 with the rest of wall 12 comprising a different wall forming composition. Capsule 26 can be a two pieced capsule comprising capsule head 27 and capsule body 28, or capsule 26 can comprise a single member, not shown. Compartment 14 contains thermo-responsive means 15 containing beneficial agent composition 16 and osmotically effective composition 17. A density member 25 is positioned between thermo-responsive composition 15 and osmotically effective solute 17. In an optional embodiment, density member 25 can be positioned immediately next to passageway 13. In this design, density member 25 is manufactured with a bore therethrough for providing a passageway for thermoresponsive beneficial agent composition to reach the exit passageway in the wall for delivery from compartment 14.

Dispenser 10 of FIGS. 1 through 6, when dispenser 10 is in operation, delivers beneficial agent formulation 16 to a warm-blooded fluid animal environment by a combination of thermodynamic and kinetic integrally performed activities. That is, in operation, heat sensitive composition 15 in response to the temperature of an animal recipient absorbs thermal energy, softens, and/or melts and forms a deliverable composition; for example, a fluidic or a semipaste like deliverable composition 15 for delivering beneficial agent composition 16 through exit means 13. As composition 15 absorbs thermal energy and undergoes change, concomitantly external fluid passes through a semipermeable wall 12 by imbibition motivated by osmotically effective solute layer 17. Fluid is imbibed in a tendency towards osmotic equilibrium to continuously produce a solution of osmotically effective solute. In a presently preferred embodiment, as solution is produced an immiscible boundary is formed between heat sensitive composition 15 and osmotically effective solute solution 17. The increase in solution causes it to occupy an increasing volume in compartment 14, thereby urging the solution to push against heat sensitive composition 15. As more solution is produced and occupies more space in compartment 14, it urges composition 15 containing agent 16 through releasing means 13. Further in operation, as seen in FIG. 6, as fluid is imbibed into device 10 through wall 12 the inner thin walled water soluble capsule member 26 dissolves at a temperature greater than 25° C., for example at animal body temperature of 37° C. or more, leaving dispenser 10 with exterior wall 12. The dissolved gelatin can lubricate the inside surface of wall 12, or it can blend with osmotically effective solute solution 17.

While FIGS. 1 through 6 are illustrative of various dispensers 10 that can be made according to the invention, it is to be understood these dispensers are not to be construed as limited, as dispenser 10 can take a wide variety of shapes, sizes and forms for delivering agent 16 to the environment of use. For example, delivery dispenser 10 can be designed for oral use for releasing a locally or systemically acting therapeutic agent in the gastrointestinal tract over time. Oral dispenser 10 can have various conventional shapes and sizes such as round with a diameter of ⅛ inch to 9/16 inches, or it can be shaped like a capsule having a range of sizes from triple zero to zero and from 1 to 8. Also, delivery dispenser 10 can be adapted, shaped, sized and structured as a buccal, cervical, intrauterine, nasal, dermal, subcutaneous, and artificial gland device. The dispenser can be used for administering a beneficial agent to animals, including warm-blooded mammals, humans, avians, reptiles and fishes. The delivery device can be used in hospitals, clinics, nursing homes, farms, zoos, veterinary clinics, sickrooms, and other environments of use.

DETAILED DESCRIPTION OF THE INVENTION

In accordance with the practice of this invention, it has now been found that wall 12 can be manufactured of a wall forming composition that does not adversely affect agent 16, an animal, or other host and in at least a part wall 12 is pervious to the passage of an external aqueous type fluid, such as water and biological fluids. In one embodiment, wall 12 can comprise in whole or in part an inert semipermeable composition. Typical semipermeable compositions comprising wall 12, in whole or in part, include semipermeable polymers known to the art as osmosis and reverse osmosis membrane, that are permeable to the passage of fluid while remaining essentially impermeable to the passage of agents, including drugs and the like. These materials are known as semipermeable homopolymers, semipermeable copolymers, and the like. In one embodiment typical materials include cellulose esters, cellulose monoesters, cellulose diesters, cellulose triesters, cellulose ethers, and cellulose ester-ethers, mixtures thereof, and the like. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkoxy, halogen, carboalkyl, alkylcarbamate, alkylcarbonate, alkylsulfonate, alkylsulfamate, and the like semipermeable polymer forming groups.

The semipermeable materials typically include a member selected from the group consisting of cellulose acylate, cellulose diacylate, cellulose triacylate; cellulose acetate; cellulose diacetate; cellulose triacetate; mono-, di- and tri-cellulose alkanylates; mono-, di- and tri-alkenylates; mono-, di- and tri-alkenylates; mono-, di- and tri-aroylates and the like. Exemplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S. of 2 to 3 and an acetyl content of 34 to 44.8% and the like. More specific cellulosic polymers include cellulose propionate having a D.S. of 1.8 and a propionyl content of 30.5%; cellulose acetate propionate having an acetyl content of 1.5 to 7% and an acetyl content of 39 to 45%; cellulose acetate propionate having an acetyl content of 2.5 to 3%, an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate; cellulose propionate morpholinobutyrate; cellulose acetate butyrate; cellulose acetate phthalate, and the like; mixed cellulose esters such as cellulose acetate valerate; cellulose acetate succinate; cellulose propionate succinate; cellulose acetate octanoate; cellulose valerate palmitate; cellulose acetate heptonate, and the like. Semipermeable polymers are known in U.S. Pat. No. 4,077,407, and they can be made by procedures described in *Encyclopedia of Polymer Science and Technology*, Vol. 3, pp 325–354, 1964, published by Interscience Publishers, Inc., New York.

Additional semipermeable polymeric compositions that are permeable to the passage of fluid and substantially impermeable to the passage of a beneficial agent formulation include acetaldehyde dimethyl cellulose acetate; cellulose acetate ethylcarbamate; cellulose acetate methylcarbamate; cellulose dimethylaminoacetate; a cellulose composition comprising cellulose acetate and hydroxypropyl methylcellulose; a composition comprising cellulose acetate and cellulose acetate butyrate; a cellulose composition comprising cellulose acetate butyrate and hydroxypropyl methylcellulose; semipermeable polyamides; semipermeable polyurethanes; semipermeable polysulfanes; semipermeable sulfonated polystyrenes; cross-linked, selectively semipermeable polymers formed by the coprecipitation of a polyanion and a polycation as disclosed in U.S. Pat. Nos. 3,173,876; 3,276,586; 3,541,005; 3,541,006 and 3,546,142; selectively semipermeable silicon rubbers; semipermeable polymers as disclosed by Loeb and Sourirajan in U.S. Pat. No. 3,133,132; semipermeable polystyrene derivatives; semipermeable (polysodiumstyrenesulfonate); semipermeable polymer exhibiting a fluid permeability of $10^{-1}$ to $10^{-7}$ (cc.mil/cm$^2$hr.atm) expressed as per atmosphere of hydrostatic or osmotic pressure difference across a semipermeable wall. The polymers are known in the art in U.S. Pat. Nos. 3,85,770; 3,916,899 and 4,160,020, and in *Handbook of Common Polymers*, by Scott, J. R., and Roff, W. J., 1971, published by CRC Press, Cleveland, Ohio.

The microporous materials used for forming a microporous wall generally can be described as having a sponge-like appearance that provides a supporting structure for interconnected pores or voids. The material can be isotropic wherein the structure is homogeneous throughout a cross-sectional area, the materials can be anisotropic wherein the structure is non-homogeneous throughout a cross-sectional area, or the materials can have both cross-sectional areas. The materials are opened-celled, as the pores are continuous or connected pores having an opening on both faces of the microporous wall. The micropores are interconnected through tortuous paths of regular and irregular shapes, including curved, linear, curved-linear, randomly oriented continuous pores, hindered connected pores and other interconnected porous paths discernible by microscopic examination.

Generally the microporous walls are characterized as having a reduced bulk density as compared to the bulk density of the corresponding non-porous precursor microporous wall. The morphological structure of the total microporous wall will have a greater proportion of total surface area than the non-porous wall. The microporous wall can be further characterized by the pore size, the number of pores, the tortuosity of the microporous paths, and the porosity which relates to the size and the number of pores. The pore size of a microporous wall is easily ascertained by measuring the observed pore diameter at the surface of the material under the electron microscope. Generally materials possessing from 5% to 95% pores, having a pore size of from 10 angstroms to 100 microns, can be used for making the wall. Relationships of the above type are discussed in *Transport Phenomena In Membranes*, by Lakshminatayamah, N., Chapter 6, 1969, published by Academic Press, Inc., New York. Microporous materials are described in *Science*, Vol. 170, pp 1302–1305, 1970; *Nature*, Vol. 214, p 285, 1967; *Polymer Engineering and Science*, Vol. 11, pp 284–388, 1971; U.S. Pat. Nos.

3,567,809 and 3,751,537; and in *Industrial Processing With Membranes,* by Lacey, R. E., and Loeb, Sidney, pp 131–134, 1972, published by Wiley Interscience, New York.

Microporous materials are commercially available and they can be made by art-known methods. The materials can be made by etched nuclear tracking; by cooling a solution of a flowable polymer below the freezing point whereby the solvent evaporates from the solution in the form of crystals dispersed in the polymer, and then curing the polymer followed by removing the solvent crystals; by cold stretching or hot stretching at low or high temperatures until pores are formed; by leaching from a polymer a soluble component by an appropriate solvent; by ion exchange reaction; and by polyelectrolyte process. In a presently preferred embodiment, the microporous wall is formed in the environment of use from a precursor microporous wall. This latter wall contains a pore-former that is removed from the precursor wall forming materials by dissolving or leaching a pore former therefrom thus forming an operable microporous wall. The pore formers used for the present purpose are a member selected from the group consisting of about 1 to 50%, or more, by weight of a solid pore-former, about 0.5 to 20% percent by weight of a liquid pore-former, and mixtures thereof. In another embodiment, the microporous wall can be formed by a compression coating technique. In this latter embodiment, a rigid microporous wall substantially free of substances soluble or swellable in the fluid present in the environment of use can be formed by compression coating a microporous material around the compartment forming ingredients. Generally a microporous wall is formed under a compression pressure of 500 to 5000 kg/cm$^2$, usually in a rotary machine. Processes for preparing microporous walls are described in *Synthetic Polymer Membranes,* by R. E. Kesting, Chapt. 4 & 5, 1971, published by McGraw-Hill, Inc.; *Chemical Reviews,* Vol. 18, pp 272–455, 1934; *Polymer Engineering and Science,* Vol. 11, pp 284–288, 1971; *J. Appln. Poly. Sci.,* Vol. 15, pp 811–829, 1971; in U.S. Pat. Nos. 3,565,259; 3,615,024; 3,751,536; 3,801,692; 3,852,224; 3,849,528 and 3,929,509, and in British Patent No. 1,459,356.

Materials suitable for forming a microporous wall include polycarbonates comprising linear polyesters of carbonic acid in which carbonate groups recur in polymer chains by phosgenation of a dihydroxy aromatic such as a bisphenol; microporous poly(vinyl chloride); microporous polyamides such as polyhexamethylene adipamide; microporous modacrylic copolymers including those formed of polyvinylchloride and acrylonitrite; styrene-acrylic acid copolymers; microporous polysulfones characterized by diphenylene sulfone groups in the linear chain thereof; halogenated polymers such as polyvinylidene fluoride; polyvinylfluoride and polyfluorohalocarbon; polychloroethers; cellulose esters; cellulose ethers; cellulose acylates, acetal polymers such as polyformaldehyde; polyesters prepared by esterification of a dicarboxylic acid or anhydride with a polyol; poly(alkylenesulfides); phenolic polyesters, microporous poly(saccharides) having substituted and unsubstituted anhydroglucose units; asymetric porous polymers; cross linked olefin polymers; hydrophobic and hydrophilic microporous homopolymers, copolymers or interpolymers having a reduce bulk density, and the materials described in U.S. Pat. Nos. 3,595,752; 3,643,178; 3,654,066; 3,709,774; 3,718,532; 3,803,061; 3,852,224; 3,852,388; 3,853,631; and 3,948,254; and in Great Britain Patent No. 1,126,849; and in *Chem. Absts.,* Vol. 71, 4274F, 22572F and 22573F, 1969.

Additional microporous materials include materials that are substantially insoluble in the fluid present in the environment of use, include microporous materials that keep their identity during operation of the dispenser, that is they do not physically or chemically change or lose their initial structure as they are inert, non-disintegrating, non-eroding and are materials that can be compressed in powder form, applied by air suspension, dipping techniques, and the like. Exemplary materials include poly(urethanes); copolymers of divinyl chloride and acrylonitrile; organic materials such as cross linked, chain extended poly(urethanes); microporous poly(urethanes) in U.S. Pat. No. 3,524,753; poly(imides); poly(benzimidazoles); collodion (cellulose nitrate with 11% nitrogen); regenerated proteins; microporous materials prepared by diffusion of a multivalent cations into polyelectrolyte sols as in U.S. Pat. No. 3,565,259; anisotropic microporous materials of ionically associated polyelectrolytes; microporous polymers formed by the coprecipitation of a polycation and a polyanion as described in U.S. Pat. Nos. 3,276,589; 3,541,006; and 3,546,142; derivatives of poly(styrene) such as poly(sodium styrene sulfone) and poly(vinylbenzyltrimethylammonium chloride); the microporous materials disclosed in U.S. Pat. Nos. 3,615,024; 3,646,178, and 3,852,224; the microporous walls having a plurality of micropores as disclosed in U.S. Pat. No. 3,948,254, and the like.

Materials that can be used for forming wall 12 when a part thereof is formed of a material free of semipermeable properties include polyethylene, polypropylene, ethylene-vinyl acetate copolymer, polybutene, polyvinyl acetate, cross-linked polyvinyl alcohol, plasticized polyamides, polyesters, polycarbonates, polyisoprene, polybutadiene, polyvinyl butyryl, and the like.

The expression, "pore-former" as used herein includes pore-forming solids and pore-forming liquids. In the later expression, the term "liquid" generically embraces semi-solids, pastes and viscous fluids. The pore-formers can be inorganic or organic. The term, "pore-former" for both solids and liquids includes substances that can be dissolved, extracted or leeched from the precursor microporous wall by fluid present in the environment of use to form an operable, open-celled type microporous wall. Additionally, the pore formers suitable for the invention include pore formers that can be dissolved, leached, eroded or extracted without causing physical or chemical changes in the polymer. The pore forming solids can have a size of about 0.1 to 200 microns and they include alkali metals salts such as lithium chloride, lithium carbonate, sodium chloride, sodium bromide, sodium carbonate, potassium chloride, potassium sulfate, potassium phosphate, sodium benzoate, sodium acetate, sodium citrate, potassium nitrate, and the like. The alkaline earth metal salts such as calcium phosphate, calcium nitrate, calcium chloride, and the like. The transition metal salts such as ferric chloride, ferrous sulfate, zinc sulfate, cupric chloride, manganese fluoride, manganese fluorosilicate, and the like. Organic compounds such as polysaccharides including sucrose, glucose, fructose, mannitol, mannose, galactose, addohexose, altrose, talose, sorbitol, and the like. Organic aliphatic ols including diols, polyols; organic ols including diols and polyols, and other polyols such as polyhydric alcohol, polyalkylene glycol, polyglycol, poly(α-ω)-alkylenediols, and the like. The pore formers are non-toxic and on their removal from the wall channels are formed through the wall that fills with fluid. The channels become, in one embodiment, means or paths for releasing a beneficial agent from the delivery device. The pores extend from the inside wall to the outside wall for effective release of beneficial agent to the exterior of the delivery system. In a presently preferred embodiment, the wall comprises 1 to 50% of pore former based on the weight of the polymer of a pore forming agent selected from the group consisting of inorganic salts, organic salts, carbohydrates and ols that are used when the pores of controlled porosity are formed during use in a biological environment.

Exemplary means 17 for delivering thermo-responsive composition 15 from dispenser 10 includes osmotically effective compounds that are also known as osmotically effective solute and osmagents. The osmagents exhibit an osmotic pressure gradient across a semipermeable wall member and imbibe fluid through the semipermeable member into dispenser 10. The osmagents attract fluid into dispenser 10 producing a solution that continuously fills dispenser 10, when it is in a fluid environment, which solution applies and exerts pressure against thermo-responsive composition 15. As pressure is applied against composition 15 it is dispensed through passageway 13 from dispenser 10. In a preferred embodiment, thermo-responsive composition 15 and osmagent solution 17 form an immiscible interface or boundary that lessens intermixing of thermixotropic composition 15 and osmagent solution 17 and also functions as a barrier means for transmitting pressure produced by osmagent solution 17 against thermixotropic composition 15. Effective osmagents useful for the present purpose include magnesium sulfate, magnesium chloride, sodium chloride, lithium chloride, potassium chloride, potassium sulfate, sodium sulfate, mannitol, urea, sorbitol, inositol, sucrose, glucose, magnesium succinate, tartaric acid, raffinose, and the like. The osmagent can be present in a layered arrangement, preferably formed under pressure. In another embodiment, the osmotic solute is initially present in excess and it can be in any physical form such as particle, crystal, pellet, tablet, strip, film or granule. The osmotic pressure of saturated solutions of various osmotically effective compounds and for mixtures of compounds at 37° C., in water, is listed in Table 1. In the table, the osmotic pressure $\pi$ is in atmospheres, ATM. The osmotic pressure is measured in a commercially available osmometer that measures the vapor pressure difference between pure water and the solution to be analyzed, and according to standard thermodynamic principles, the vapor pressure ratio is converted into osmotic pressure difference. In Table 1, osmotic pressures of from 20 ATM to 500 ATM are set forth; of course, the invention includes the use of lower osmotic pressures from zero, and higher osmotic pressures than those set forth by way of example in Table 1. The amount of osmagent initially present in dispenser 10 is from 125 mg to 25 g, or more. The osmometer used for the present measurements is identified as Model 320B Vapor Pressure Osmometer, manufactured by the Hewlett Packard Co., Avondale, Pa.

TABLE 1

| COMPOUND OR MIXTURE | OSMOTIC PRESSURE ATM |
|---|---|
| Lactose-Fructose | 500 |

TABLE 1-continued

| COMPOUND OR MIXTURE | OSMOTIC PRESSURE ATM |
|---|---|
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Dextrose | 82 |
| Potassium Sulfate | 39 |
| Mannitol | 38 |
| Sodium Phosphate Tribasic.12H$_2$O | 36 |
| Sodium Phosphate Dibasic.7H$_2$O | 31 |
| Sodium Phosphate Dibasic.12H$_2$O | 31 |
| Sodium Phosphate Dibasic Anhydrous | 29 |
| Sodium Phosphate Monobasic.H$_2$O | 28 |

The term, "thermo-responsive" as used herein denotes a composition of matter that, in the presence of thermal energy or heat, absorbs or takes-up the heat and changes its physical form. The generic term, "thermo-responsive" includes also thermo-plastic compositions comprising means capable for softening, or melting, or becoming dispensable in response to heat and solidifying or thickening again when cooled. The generic term includes also thermotropic compositions capable of undergoing change in response to the application of thermal energy in a gradient manner and they are temperature sensitive in their response to the application or the withdrawl of thermal energy. The term, "thermixotropic" has a similar meaning in the dispensing art and it indicates a composition that exhibits the property of absorbing heat and changing from a storage state to a dispensable state in situ. The thermo-responsive composition as used for the purposes of this invention, in a preferred embodiment, denotes the physical-chemical property of a composition agent carrier to exhibit solid, or solid-like, properties at temperatures up to 25° C., and become fluid, semisolid, or viscous when contacted by heat at temperatures from 25° C. to 65° C., usually in the range of 30° C. to 45° C., and more preferably at animal temperatures of 37° C. to 42° C. The thermo-responsive carrier is heat-sensitive and preferably anhydrous and it has the property of melting, dissolving, undergoing dissolution, softening, or liquifying at the elevated temperatures, thereby making it possible for the dispenser 10 to deliver the thermo-responsive carrier 15 with beneficial agent 16 homogeneously or heterogeneously blended therein. The thermo-responsive carrier can be lipophilic, hydrophilic or hydrophobic. Another important property of the carrier is its ability to maintain the stability of the agent contained therein during storage and during delivery of the agent. The present invention uses the phrases, "melting point", "softening point", "pour point", or "liquifies", to indicate the temperature at which the thermo-responsive composition melts, undergoes dissolution, or forms a paste-like ribbon, dissolves to form a dispensable carrier so it can be used for dispensing beneficial agent 16 from a dispenser 10. Representative thermo-responsive compositions and their melting points are as follows: cocoa butter, 32°-34° C.; cocoa butter plus 2% beeswax, 35°-37° C.; propylene glycol monostearate and distearate, 32°-35° C.; hydrogenated oils such as hydrogenated vegetable oil, 36°–37.5° C.; 80% hydrogenated vegetable oil and 20% sorbitan monopalmitate, 39°–39.5° C.; 80% hydrogenated vegetable oil and 20% polysorbate 60, 36°–37° C.; 77.5% hydrogenated vegetable oil, 20% sorbitan trioleate and 2.5% beeswax, 35°–36° C.; 72.5% hydrogenated vegetable oil, 20% sorbitan trioleate, 2.5% beeswax and 5.0% distilled water, 37°–38° C.; mono-, di-, and triglycerides of acids having from 8-22 carbon atoms including saturated and unsaturated acids such as palmitic, stearic, oleic, linoleic, linolenic and archidonic; glycerides of fatty acids having a melting point of at least 32° C. such as monoglycerides, diglycerides and triglycerides of vegetable fatty acids having 10 to 18 carbon atoms obtained from coconut oil, olive oil and the like; partially hydrogenated cottonseed oil 35°–39° C.; hardened fatty alcohols and fats, 33°–36° C.; hexadienol and anhydrous lanolin thiethanolamine glyceryl monostearate, 38° C.; eutetic mixtures of mono-, di-, and triglycerides, 35°–39° C.; Witepsol ® #15, triglyceride of saturated vegetable fatty acid with monoglycerides, 33.5°–35.5° C.; Witepsol ® H32 free of hydroxyl groups, 31°–33° C.; Witepsol ® W25 having a saponification value of 225-240 and a melting point of 33.5°–35.5° C.; Witepsol ® E75 having a saponification value of 220-230 and a melting point of 37°–39° C.; a polyalkylene glycol such as polyethylene glycol 1000, a linear polymer of ethylene oxide, 38°–41° C.; polyethylene glycol 1500, melting at 38°–41° C.; polyethylene glycol monostearate, 39°–42.5° C.; 33% polyethylene glycol 1500, 47% polyethylene glycol 6000 and 20% distilled water, 39°–41° C.; 30% polyethylene glycol 1500, 40% polyethylene glycol 4000 and 30% polyethylene glycol 400, 33°–38° C.; mixture of mono-, di-, and triglycerides of saturated fatty acids having 11 to 17 carbon atoms, 33°–35° C.; block polymer of 1,2-butylene oxide and ethylene oxide; block polymer of propylene oxide and ethylene oxide; block polymer of polyoxyalkylene and propylene glycol; inert, food grade multiwax composition that is soft at 25° C. and continually softens as the temperature rises from 25° C. to 45° C. and is dispensable in response to a hydrostatic pressure of 8 to 12 psi, and the like. The thermo-responsive composition is a means for storing a beneficial agent preferably as a solid composition at a temperature up to 25° C., and in operation for maintaining an immiscible boundary at the thermo-responsive-osmotic interface formed during dispensing the agent in a dispensable composition at a temperature greater than 25° C., and preferably in the range of 30° to 45° C. The thermo-responsive composition on being dispensed into a biological environment is easily excreted, metabolized, assimilated, or the like, for effective use of the beneficial agent.

Materials useful for forming the internal wall member are materials used for forming a capsule. The capsule wall member generally comprises a single piece or two-piece construction, and in a presently preferred embodiment it is tubular shaped and it has a mouth at one end, and at the end distant therefrom it is closed in a hemispherical or dome shaped end. The capsule member serves as a hollow body having a wall that surrounds and defines an interior compartment provided with an opening for establishing communication with the exterior of the capsule and for filling the capsule. In one embodiment a capsule is made by dipping a mandrel, such as a stainless steel mandrel, into a bath containing a solution of a capsule wall forming material to coat the mandrel with the material. Then, the mandrel is withdrawn, cooled and dried in a current of air. The capsule is stripped from the mandrel and trimmed to yield a capsule with an internal lumen. Materials used for forming capsules are the commercially available materials including gelatin, gelatin having a viscosity of 15 to 30 millipoises and a bloom strength up to 150 grams; gelatin having a bloom value of 160 to 250; a composition comprising gelatin, erythrosin, iron oxide and titanium dioxide; a composition comprising gelatin, glycerine, sorbitol, potassium sorbate and titanium dioxide; a composition comprising gelatin, acacia, glycerin and water; water soluble polymers that permit the transport of water therethrough and can be made into capsules, and the like.

The expression, "beneficial agent" as used herein denotes any beneficial agent or compound that can be delivered by device 10 to produce a beneficial and useful result. The beneficial agent can be from insoluble to very soluble in the heat sensitive carrier means 15. The term, "beneficial agent" includes biocide, parasiticide, flukicide, fungicide, medicine or drug, larvicide, nutrient, vitamin, growth promotant, growth permittant, efficiency factors, food supplement, mineral, anthelmintic, vaccines and other agents that benefit the environment of use.

In the specification and the accompanying claims, the term, "beneficial agent" includes any physiologically or pharmacologically active substances that produce a local or systemic effect in animals, including warm-blooded mammals; humans and primates; household, sport, farm and zoo animals. The term, "physiologically" as used herein denotes the administration of a drug to produce normal levels and functions. The term, "pharmacologically" denotes variations in response to an amount of drug administered to the host. *Stedman's Medical Dictionary*, 1966, published by Williams and Wilkins, Baltimore, Md. The beneficially active drugs 17 that can be delivered by device 10 include inorganic and organic drugs, such as drugs that act on the central nervous system, depressants, hypnotics, sedatives, psychic energizers, tranquilizers, anticonvulsants, muscle relaxants, antiparkinson agents, analgesic, anti-inflammatory, anesthetics, muscle contractants, antimicrobials, antimalarials, hormonal agents, contraceptives, diuretics, sympathomimetics, antiparasitics, neoplastics, hypoglycemics, opthalmics, electrolytes, cardiovascular drugs and the like.

Exemplary drugs that can be delivered by the delivery device are prochlorperazine edisylate, ferrous sulfate, animocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, pilocarpine hydrochloride, atropine sulfate, methascopolamine bromide, isopramide iodide, tridehexethyl chloride, phenformin hydrochloride, methylphenidate hydrochloride, oxprenolol hydrochloride, metroprolol tartrate, cimetidine hydrochloride, diphenidol, meclizine hydrochloride, prochlorperazine maleate, phenoxybenzamine, thiethylperazine maleate, anisindone, diphenadione, erythrityl tetranitrate, dizoxin, isofurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, esterogenic steroids, progestational steriods, corticosteroids, hydrocortisone, 17 β-estradiol, ethenyl estradiol, ethinyl estradiol 3-methyl ester, prednisolone, hydrocorticosterone acetate, triamcinolone, methyltesterone, 17 α-hydroxyprogesterone acetate, 19-nor-progesterone, norgestrel, norethindone, norethiderone, progesterone, norgesterone, norethynodrel, and the like.

Examples of other beneficial drugs that can be delivered by the delivery device include aspirin, indomethacin, naproxen, fenoprofen, sulindac, diclofenac, indoprofen, nitroglycerin, propanolol, valproate, timolol, atenolol, alprenolol, cimetidine, clonidine, imipramine, levodopa, chloropromazine, reserpine, methyl-dopa, dihyroxyphenylalanine, prvaloxyloxyethyl ester of α-methyldopa hydrochloride, theophylline, calcium gluconate, ferrous lactate, vincamine, diazepam, phenoxybenzamine, blocking agents, and the like. The beneficial drugs are known to the art in *Pharmaceutical Sciences,* by Remington, 14th Ed., 1979, published by Mack Publishing Co., Easton, Pa.; *The Drug, The Nurse, The Patient, Including Current Drug Handbook,* 1974–1976, by Falconer et al, published by Sunder Co., Philadelphia, Pa., and *Medical Chemistry,* 3rd Ed., Vol. 1 & 2, by Burger, published by Wiley-Interscience, New York.

Representative of beneficial medicaments that can be delivered to warm-blooded animals, exemplified by ruminants, using the delivery system of this invention, include anthelmintics such as mebendazole, levamisole, albendazole, cambendazole, fenbendazole, parbendazole, oxfendazole, oxybendazole, thiabendazole, tichlorfon, praziquantel, morantel and parantel, and the like; antiparasitic agents such as avermectin and ivermectin, as disclosed in U.S. Pat. Nos. 4,199,569 and 4,339,397, both assigned to Merck & Co., and in *Science,* Vol. 221, pp 823–828, 1983, wherein said ivermectin antiparasitic drugs are disclosed as useful for aiding in controlling commonly occurring infestations in animals, such as roundworms, lung worms, and the like, and said ivermectin also being useful for the management of insect infestations such as grub, lice, mange mite, and the like; antimicrobial agents such as chlortetracycline, oxytetracycline, tetracycline, gentamicin, streptomycin, dihydrostreptomycin, bacitracins, erthromycin, ampicillins, penicillins, cephalosporins, and the like; sulfa drugs such as sulfamethazine, sulfathiazole, and the like; growth stimulants such as Monesin ® sodium and Elfazepam ®; defleaing agents such as dexamethazone and flumethazone; rumen fermentation manipulators and ionophores such as lasalocid, virginiamycin, salinomycin and ronnel; minerals, including copper oxide, cobalt sulphate, potassium iodate, zinc oxide, manganese sulphate, zinc sulphate, silenium, sodium selenite, potassium selenite, beneficial mineral salts, and the like; anti-bloat agents such as organopoly siloxanes; hormone growth supplements such as stilbestrol; vitamines such as vitamines A and D comprising 500,000:100,000 ius/g, vitamin E comprising 500,000 ius/g, and the like; antienteritis agents such as furazolidone; growth efficiency factors; nutritional supplements such as lysine monohydrochloride, methionine, magnesium carbonate, and the like; β-agonists, elenbuterol and the like; chemical markers such as chromic oxide, and salts of ytterbium and erbium.

The agent or drug can be in various forms, such as uncharged molecules, molecular complexes, pharmacologically acceptable salts such as hydrochlorides, hydro-bromide, sulfate, laurylate, palmitate, phosphate, nitrate, borate, acetate, maleate, tartrate, oleate, salicylate, and the like. For acid drugs, salts of metals, amines, or organic cations, for example, quaternary ammonium can be used. Derivatives of agents or drugs such as esters, ethers, amides, and the like, can be used. Also, a drug or agent that is lipid insoluble can be used neat or in a form that is a lipid soluble derivative thereof, and on its release from the device can be converted by body activities to biologically active forms. Agents and drugs that are water insoluble can be in form that is converted by enzymes, hydrolyzed by body pH or other metabolic processes, to the original biologically active form. The amount of drug present in a device is initially, in a present embodiment, an amount in excess of the amount that can be dissolved in the heat sensitive formulation. Generally, the device can contain from 0.05 ng to 5 g or more, with individual devices containing, for example, 25 ng, 1 mg, 5 mg, 125 mg, 250 mg, 500 mg, 750 mg, 1.5 g, 10 g, 25 g, 50 g, and the like. The device can dispense from 10 ng to 1500 mg per day or higher over a prolonged period of time.

In those embodiments when an active agent including a drug is insoluble in the thermixotropic carrier, in a presently preferred embodiment a surfactant is advantageously added to the thermixotropic active agent composition to enhance the stability and the dispensability of the composition The surfactant must be inert to the active agent as well as biologically inert and, accordingly, non-ionic surfactants are preferred. Exemplary non-ionic surfactants include sorbitan monostearate, polysorbate 80 USP [polyoxyethylene (20) sorbitan monooleate], and polyoxyethylene 4 stearate. Several active agent-surfactant combinations have been found to be particularly effective; for example, sorbitan monostearate has been found effective to stabilize suspensions of tetracycline, while polyoxyethylene sorbitan monooleate has likewise been found suitable for use with chloramphenicol. A preferred range for the surfactant is typically between about 0.1 and 5 percent by weight of the total mix.

The thermixotropic beneficial agent composition optionally may include an anti-oxidant to prevent degradation during the prolonged periods of storage now made possible, usually in an amount of from about 0.01 to about 2 percent by weight of the active agent. Any of the food-approved anti-oxidants may be employed in this capacity, with the following being merely illustrative in this regard: tertiary -butyl-4-methoxyphenol (mixture of 2- and 3-isomers), 2,6-ditertiary butyl-p-cresol, propyl gallate, 6-ethoxy-1,2-dihydro-2,2,4-trimethylquinoline (ethoxyquin) and nordihydroguaiaretic acid (NDGA).

The walls, including the semipermeable wall, the microporous wall and the laminated wall can be formed by molding, air spraying, dipping or brushing with a wall forming composition. Other and presently preferred techniques that can be used for applying wall forming materials are the air suspension procedure and the pan coating procedures. The air procedure consists in suspending and tumbling the compartment forming materials in a current of air and a wall forming composition until the wall surrounds and coats the materials. The procedure can be repeated with a different wall forming composition to form a laminated wall. The air suspension procedure is described in U.S. Pat. No. 2,799,241; *J. Am. Pharm. Assoc.,* Vol. 48, pp 451–459, 1979; and ibid, Vol. 39, pp 82–84, 1960. Other standard manufacturing procedures are described in *Modern Plastics Encyclopedia,* Vol. 46, pp 62–70, 1969; and in *Pharmaceutical Sciences,* by Remington, 14th Ed., pp 1626–2678, 1970, published by Mack Publishing Co., Easton, Pa.

Exemplary solvents suitable for manufacturing the walls include inert inorganic and organic solvents that do not adversely harm the materials, the wall, the beneficial agent, the thermo-responsive composition, the expandable member, and the final dispenser. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, ethyl acetate, isopropyl acetate, n-gutyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachlorethane, ethyl ether, isopropyl ether, cyclohexane, cyclo-octane, benzene, toluene, naptha, 1,4-dopxame. tetrahydrofuran, diglyme, water, and mixtures thereof such as acetone and water, acetone and methanol, acetone and ethyl alcohol, methylene dichloride and methanol, and ethylene dichloride and methanol. Generally, for the present purpose the wall is applied at a temperature a few degrees less than the melting point of the thermo-responsive composition. Or, the thermoplastic composition can be loaded into the dispenser after applying the wall.

The expression, "means for releasing a beneficial agent" as used herein includes at least one preformed passageway, or at least one passageway formed when the device is in use. The passageway in either embodiment will pass through the wall for communicating with the compartment for releasing the beneficial agent from the device. The expression, "means for releasing a beneficial agent" includes passageway aperture, bore, pore, porous element through which the beneficial agent can migrate, hollow fiber, capillary tube, and the like. The means includes a material that is removed from the wall during use such as eroding in the environment of use to produce at least one passageway in the device. Representative materials suitable for forming a passageway include erodible poly(glycolic), poly(lactic) in the wall, gelatinous filaments, poly(vinyl alcohol), and the like. The passageway can be formed by leaching a material such as sorbitol from the wall. The passageway can have any shape such as round, triangular, square, elliptical, irregular, and the like. The device can be constructed with more than one passageway, especially for dispensing released agent over a wide area. In a preferred embodiment, when the device is fabricated with more than one passageway, they can be constructed as the functional equivalent of a single passageway. The passageway can be formed also by mechanical drilling or laser drilling through the wall. A description of means for releasing a beneficial agent as described herein is disclosed in U.S. Pat. Nos. 3,845,770 and 3,916,899. Procedures for forming at least one passageway and for providing multiporous passageways of governed porosity by leaching from a cellulose wall a pore former is disclosed in U.S. Pat. Nos. 4,200,098; 4,235,236; 4,309,996, and 4,320,759. The leaching or dissolving of a pore former from a wall forming material is known also in U.S. Pat. Nos. 4,256,108; 4,265,874, and 4,344,929. Laser drilling equipment having photo detection means for orienting a device for selecting a surface for drilling a passageway for communicating with a preselected area inside a device is known in U.S. Pat. Nos. 4,063,064 and 4,088,864.

DESCRIPTION OF EXAMPLES OF THE INVENTION

The following examples are merely illustrative of the present invention and they should not be construed as limiting the scope of the invention in any way, as these examples and other equivalents thereof will become more apparent to those skilled in the art in the light of the present disclosure, the drawings and the accompanying claims.

EXAMPLE 1

First, 1000 milligrams of tetracycline hydrochloride; 650 milligrams of poly(ethylene glycol-600), 335 milligrams of poly(ethylene glycol-1000), 1.2 milligrams of sorbitan monostearate and 0.02 milligrams of 2,6-ditertiary butyl-p-cresol are homogeneously blended at 39° C. for 20 minutes with constant stirring of the ingredients. Then, the heated blend is poured into an opened mouth capsule and allowed to cool to room temperature. Next, an osmotic tablet comprising sodium chloride is placed into the opened end of the capsule until the osmagent contacts the thermixotropic composition to provide the laminate of FIG. 7. The tablet has a shape that corresponds to the shape of the inside of the capsule. Next, the capsule is coated in a pan coater with a wall comprising 1.8 grams of 91% cellulose acetae butyrate and 9% poly(ethylene glycol 400). The wall is coated onto the capsule from a 5% wt/wt solution in methylene chloride methanol 90:10 v/v solvent system. The wall coated dispenser is dried at 24° C. in a current of dry air for 72 hours. Next, a 20 mil exit passageway is drilled through the outside wall using a high speed mechanical drill for connecting the exterior of the dispenser with the heat-sensitive drug composition. In a fluid, warm environment, the dispenser deliver the drug over time to the environment.

EXAMPLE 2

First, 6000 milligrams of chloramphenical, 5000 milligrams of cocoa butter, and 44 milligrams of polyoxyethylene sorbitan monooleate are homogeneously blended at 39° C. and then cooled to room temperature of 35° C. Then, the blend is milled twice in an Astra mill, reheated and poured into a mold having a tablet-like shape. Next, 5000 milligrams of sodium chloride, 1000 milligrams of tartaric acid and 10 mg binder polyvinyl pyrrolidone are blended to form a homogeneous blend, and then compression fed into a tablet press and pressed at a pressure of 1½ tons. Then, the two tablets are placed together in laminar arrangement and dip coated with an external wall of cellulose acetate having an acetyl content of 32%. A 5% polymer solution in methylene chloride-methanol 90:10 wt/wt is used to form the exterior wall. A passageway is laser drilled having a diameter of 15 mils through the wall for delivering the drug from the dispenser.

EXAMPLE 3

First, 240 milligrams of levamisole hydrochloride, 440 milligrams of copper oxide, 1.2 milligrams of cobalt sulfate, 0.5 milligrams of sodium selenite, 2.1 milligrams of potassium iodate, 77.2 milligrams of zinc oxide, 16.5 milligrams of vitamins A and D (500,000:100,000 ius/g), 16.5 milligrams of vitamin E (500,000 ius/g), 1.5 milligrams of magnesium sulphate, 5.0 milligrams of zinc sulphate, 10,000 milligrams of cocoa butter and 100 milligrams of sorbitan monostearate are heat blended with stirring to produce a homogeneous composition. The heated composition is poured into a mold and permitted to cool. Next, a layer of a composition comprising sodium chloride and urea is added to the mold in contacting position and pressed to form a compartment forming member. Then, the laminated arrangement is coated by dipping it quickly into a microporous wall forming composition consisting essentially of 45% by weight of cellulose acetate having an acetyl content of 39.8%, 45% by weight of sorbitol and 10% by weight of polyethylene glycol 400. Then, a semipermeable wall is coated onto a part of the microporous wall, except for an uncoated beneficial agent releasing surface that is in immediate contact with the thermixotropic composition in the compartment. The semipermeable wall comprises 50% by weight of cellulose acetate having an acetyl content of 39.8% and 50% by weight of cellulose acetate having an acetyl content of 32%.

EXAMPLE 4

A dispenser manufactured in the shape of an oral dispenser for the controlled delivery of indomethacin is made as follows: First, 300 milligrams of commercially available Butronic ® L-1 polyol, a block polymer formed by the polymerization of 1,2-butylene oxide to which ethylene oxide is added, as reported in *Cosmetics and Toiletries*, Vol. 97, pp 61-67, 1982, which polymer flows at a pour point of 39° C., is melted at 55° C. and then 200 milligrams of indomethacin is added thereto using a high sheer ultrasonic mixer. The resulting mixture is placed in a vacuum oven at 55° C. and the pressure reduced to less than 10 mm of mercury. The composition is allowed to remain in the vacuum for a period of about 10 minutes for removing entrapped air. Next, 400 milligrams of the resulting heat-sensitive thermoplastic drug formulation is poured into a ½ oz opened mouth gelatin capsule. Then, a thin film of polyamide-66 having a shape corresponding to the inside of the capsule is placed therein in contact with the drug containing composition. Next, an osmagent composition comprising 300 milligrams of dried sodium chloride formed as a tablet under 3½ tons of compression force is placed inside the capsule in contact with the polyamide film. Then, the capsule is coated in a pan coater with a rate controlling wall comprising 1.8 grams of 91% cellulose acetate butyrate and 9% polyethylene glycol 400. The wall is coated from a 5% solution of methylene chloride:methanol, 90:10 v/v. The wall coated drug delivery systems are dried at 35° C. for 24 hours in a current of dry air. Next, a 25 mil exit passageway is drilled through the wall for communicating with the drug formulation. The passageway establishes communication with the heat-responsive drug formulation for delivering it from the delivery system over time in the gastrointestinal tract of a warmblooded mammal.

EXAMPLE 5

A dispensing system manufactured in the shape of a dispenser for the controlled delivery of ivermectin is made as follows: First, 193 g of Butronic ® L-1 polyol, a block polymer formed by the polmerization of 1,2-butylene oxide to which ethylene oxide is added, as reported in *Cosmetics and Toiletries*, Vol. 97, pp 61-66, which polymer flow at a pour point of 39° C., is melted at 55° C., and then 13.98 g of ivermectin is added thereto using a high sheer ultrasonic mixer. The resulting mixture is placed in a vacuum oven at 55° C. and the pressure reduced to less than 10 mm of mercury. The ivermectin Butronic ® composition is allowed to remain in the vacuum for a period of about 10 minutes, for removing entrapped air. Next, 4 g of the resulting thermoplastic drug formulation is poured into a gelatin capsule charged with a 33 g stainless steel density member having a bore therethrough. Then, a solution producing member, having a shape corresponding to the inside of the capsule, is placed inside the capsule in contact with the thermoplastic ivermectin drug formulation. The solution producing member comprises the osmotically active means sodium chloride pressed as a core for placing in the capsule. Next, the capsule is coated in a pan coater with a rate controlling wall comprising 1.8 g of 91% cellulose acetate butyrate and 9% polyethylene glycol 400. The wall is coated from a 5% wt/wt solution in methylene chloride methanol 90:10 v/v solvent system. The wall coated delivery systems then are dried at 20° C. for 24 hours in a current of dry air. Next, a 30 mil passageway is drilled through the wall using a high speed mechanical drill for communicating the passageway with the bore. The passageway bore arrangement established communication with the heat-responsive drug formulation for delivering it from the delivery system. The dispenser made according to this example has an average release rate of 0.6 mg per hour over a 480 hour period of time.

EXAMPLE 6

Figure 7:
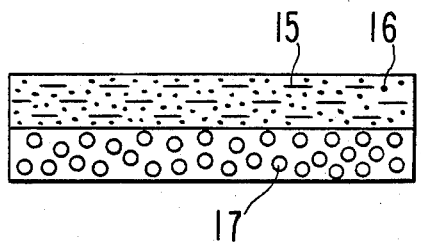

A dispensing system manufactured in the shape of a dispenser for the controlled delivery of ivermectin, copper oxide, vitamins A and D, is made as follows: First, 193 g of Butronic ® L-1 polyol, a block polymer formed by the polymerization of 1,2-butylene oxide to which ethylene oxide is added, as reported in *Cosmetics and Toiletries*, ibid, which polymer flow at a pour point of 39° C., is melted at 55° C., and then 13.98 g of ivermectin, 44 g of copper oxide needles, 1.65 g of vitamins A and D are added thereto using a high sheer ultrasonic mixer. The resulting mixture is placed in a vacuum oven at 55° C. and the pressure reduced to less than 10 mm of mercury. The ivermectin Butronic ® composition is allowed to remain in the vacuum for a period of about 10 minutes, for removing entrapped air. Next, 4 g of the resulting thermoplastic drug formulation is poured into a mold and cooled to room temperature. Then, an osmotically active means composition comprising sodium chloride and tartaric acid is added to the mold and pressure applied thereto to form a laminate arrangement comprising a thermixotropic composition 15 containing the active agents 16 in laminar arrangement with the osmotic active means 17 as seen in FIG. 7. Next, the laminate is removed from the mold and coated by dipping the laminate into a rate controlling wall forming composition comprising 1.8 g of 91% cellulose acetate butyrate and 9% polyethylene glycol 400. The wall is coated from a 5% wt/wt solution in methylene chloride methanol 90:10 v/v solvent system. The wall coated delivery systems are dried at 20° C. for 24 hours in a current of dry air. Next, a 30 mil passageway is drilled through the wall for connecting the compartment with the exterior of the device for releasing the beneficial agents to the environment of use over time.

EXAMPLE 7

A dispensing system is prepared for manufacturing a dispenser according to the procedure of Example 6, with the conditions as previously set forth, except that in this example the thermo-responsive composition comprises a food grade multiwax that is soft at a temperature of 25° C. and softens in the presence of rising temperatures from 25° C. to 40° C. and can be dispensed from the dispenser system under a hydrostatic pressure of 8 to 12 psi.

EXAMPLE 8

A dispensing system is prepared for manufacturing a dispenser according to the procedure of Example 6, with the conditions as previously set forth, except that in this example the thermo-responsive composition comprises a food grade multiwax that is soft at a temperature of 25° C. and softens in the presence of rising temperatures from 25° C. to 40° C. and can be dispensed from the dispenser system under a hydrostatic pressure of 8 to 12 psi, and the beneficial agents comprise a mixture of minerals and vitamins in stated percentages: 40 copper oxide. 0.2 cobalt sulphate, 0.1 sodium selenite, 0.4 potassium iodate, 14 zinc oxide, 2 vitamin A, 2 vitamin D, 3 vitamin E, 29 manganese sulphate and 10 zinc sulphate.

EXAMPLE 9

A dispensing system is provided according to the above examples, wherein the dispensing system comprises oxfendazole for administering to an animal in need of an anthelmintic.

An embodiment of the invention pertains to a method for administering a beneficial agent, drug, nutrient, and the like, at a controlled rate to an animal, which method comprises the steps of: (a) admitting orally into the animal a dispenser comprising: (1) comprising in at least a part a polymeric composition permeable to the passage of fluid, the wall surrounding: (2) an internal lumen containing a layer of a beneficial drug formulation comprising a dosage unit amount of drug for preforming a beneficial program in a heat-sensitive pharmaceutically acceptable carrier that melts at body temperature and is a means for transporting the drug from the dispenser; (3) a layer of an osmagent for forming a solution in the lumen; and (4) at least one dispensing means through the wall communicating with the heat-sensitive drug formulation; (b) imbibing fluid through the wall at a rate determined by the permeability of the wall and the osmotic pressure gradient across the wall causing the osmagent to form a solution and fill the lumen; (c) melting the drug formulation to form a flowable formulation; and (d) delivering the beneficial drug formulation from the lumen by the solution continually filling the lumen and thereby exerting pressure against the melting formulation causing the formulation to be dispensed in a therapeutically effective amount through the dispensing means at a controlled rate to the animal over a prolonged period of time.

It will be readily appreciated the present invention contributes to the dispensing art to unobvious dispenser have wide and practical application. The invention comprising a heat-sensitive means and a solution forming means operating together for dispensing a beneficial agent at a controlled rate. It is unobvious, as it is unexpected that a pair of means could physically change with one means forming a dispensable composition that is urged simultaneously by the solution forming means from the device over time. In as much as the foregoing specification comprises preferred embodiments of the invention, it is understood that variations and modifications may be made herein in accordance with the inventive principles disclosed, without departing from the scope of the invention.

We claim:

1. A dispenser for delivering avermectin to an environment of use, the dispenser comprising:
   (a) wall means for surrounding and forming a compartment, which compartment comprises;
      (1) lipophilic means for absorbing thermal energy from the enviroment of use;
      (2) a beneficially effective amount of avermectin present in the means for absorbing thermal energy;
      (3) osmotically active means for mixing with an aqueous fluid present in the environment of use that enters the compartment for increasing the aqueous solution volume in the compartment; and,
   (b) means in the wall for delivering avermectin from the dispenser to the environment of use over time.

2. The dispenser for delivering avermectin to the environment of use according to claim 1, wherein the avermectin is ivermectin.

3. The dispenser for delivering avermectin to the environment of use according to claim 1, wherein the wall means comprises a composition permeable to the passage of fluid.

4. The dispenser for delivering avermectin to the environment of use according to claim 1, wherein the means in the wall for delivering avermectin comprises at least one passageway formed when the dispenser is in use.

5. The dispenser for delivering avermectin to the environment of use according to claim 1, wherein the means in the wall for dispensing avermectin comprises at least one passageway formed when the dispenser is in use, and wherein the avermectin is an ivermectin.

6. The dispenser for delivering avermectin to the environment of use according to claim 1, wherein the means in the wall for delivering avermectin comprises a passageway forming material that is removed from the wall when the dispenser is in operation in the environment of use.

7. The dispenser for delivering avermectin to the environment of use according to claim 1, wherein the wall means comprise a microporous composition.

8. The dispenser for delivering avermectin to the environment of use according to claim 1, wherein the wall means comprises a microporous composition laminated in part by a semipermeable composition.

9. The dispenser for delivering avermectin to the environment of use according to claim 1, wherein the wall means comprises a semipermeable composition.

10. The dispenser for delivering avermectin to the environment of use according to claim 1, wherein the wall means comprise a polymeric composition comprising a pore former that is removed from the composition, when the dispenser is in operation in a fluid environment, to form a multiplicity of controlled porosity pores for releasing avermectin from the dispenser.

11. The dispenser for delivering avermectin to the environment of use according to claim 1, wherein osmotically active means for mixing with fluid is an osmagent that mixes with fluid that enters the compartment and continuously forms an aqueous solution.

12. The dispenser for delivering avermectin to the environment of use according to claim 1, wherein the means for absorbing thermal energy forms a dispensable composition at a temperature of from 25° C. to 45° C.

13. The dispenser for delivering avermectin to the environment of use according to claim 1, wherein when the dispenser is in operation in the environment of use, the means for absorbing thermal energy absorbs heat from the environment and forms a dispensable composition, and the osmotically active means imbibes fluid and forms an aqueous solution in the compartment.

14. The dispenser for delivering avermectin to the environment of use according to claim 1, wherein, the dispenser is in operation in the environment of use, the means for absorbing thermal energy absorbs thermal energy and forms a dispensable composition, the means for forming a solution imbibes fluid and forms a solution in the compartment, and the dispensable composition and the solution form in situ a substantially immiscible interface therebetween.

15. The dispenser for delivering avermectin to the environment of use according to claim 1, wherein the wall means that surrounds and forms the internal compartment comprises a member selected from the group consisting of an olefin polymer, a condensation polymer, a silicon polymer, and a carbohydrate polymer.

16. The dispenser for delivering avermectin to the environment of use according to claim 1, wherein a film is positioned between the means for absorbing thermal energy and the osmotically active means.

17. The dispenser for delivering avermectin to the environment of use according to claim 1, wherein the compartment comprises a layer of the means for absorbing thermal energy comprising avermectin.

18. The dispenser for delivering avermectin to the environment of use according to claim 1, wherein the compartment comprises a layer of the osmotically active means.

19. A dispenser for delivering a beneficial agent composition to a biological environment of use, the dispenser comprising
 (a) wall means that surrounds and defines an internal compartment;
 (b) means in the compartment for mixing with a beneficial agent, said means capable of changing its physical form in the presence of absorbed thermal energy from the biological environment of use;
 (c) a beneficial agent mixed in the means for absorbing thermal energy;
 (d) means in the compartment for imbibing an aqueous fluid present in the environment of use into the dispenser for forming continously an aqueous solution with the fluid that enters the compartment from the biological environment of use; and,
 (e) means in the wall for dispensing the beneficial agent formulation from the dispenser to the biological environment of use over time.

20. The dispenser for delivering a beneficial agent composition to the biological environment of use according to claim 19, wherein the wall means that surrounds and defines an internal compartment comprises at least in part a composition permeable to the passage of an external fluid.

21. The dispenser for delivering a beneficial agent composition to the biological environment of use according to claim 19, wherein the means in the compartment for absorbing energy is in layered arrangement with the means for forming a solution.

22. The dispenser for delivering a beneficial agent composition to the biological environment of use according to claim 19, wherein the means for continuously forming a solution in the compartment comprises an osmagent that is substantially dry when the dispenser is initially admitted into the biological environment of use.

23. The dispenser for delivering a beneficial agent composition to the biological environment of use according to claim 19, wherein the wall means that surrounds and defines the compartment comprises a first polymeric composition that permits the passage of fluid present in the environment of use and is substantially impervious to the passage of a beneficial agent, and a second polymeric composition that permits the passage of beneficial agent formulation from the dispenser.

24. The dispenser for delivering a beneficial agent composition to the biological environment of use according to claim 19, wherein the means in the wall for dispensing the beneficial agent formulation comprises at least one passageway.

25. The dispenser for delivering a beneficial agent composition to the biological environment of use according to claim 19, wherein the means in the wall for dispensing the beneficial agent formulation comprises at least one passageway formed when the dispenser is in use.

26. The dispenser for delivering a beneficial agent composition to the biological environment of use according to claim 19, wherein the means in the wall for delivering the beneficial agent formulation from the dispenser comprises a passageway forming material that is removed from the means when the dispenser is in operation in the environment of use.

27. The dispenser for delivering a beneficial agent composition to the biological environment of use according to claim 19, wherein the means in the wall for delivering the beneficial agent is a passageway connecting the exterior of the dispenser with the inside of the dispenser.

28. The dispenser for delivering a beneficial agent composition to the biological environment of use according to claim 19, wherein the wall means that surrounds and defines the compartment comprises a microporous member laminated in part by a semipermeable member.

29. The dispenser for delivering a beneficial agent composition to the biological environment of use according to claim 19, wherein the wall means that surrounds and defines the compartment comprises a microporous member laminated by a semipermeable member with a passageway through the semipermeable wall in agent releasing position with a releasing pore in the microporous member.

30. The dispenser for delivering a beneficial agent composition to the biological environment of use according to claim 19, wherein the means in the compartment for absorbing thermal energy forms a dispensable composition at a temperature of 30° C. to 45° C.

31. The dispenser for delivering a beneficial agent composition to the biological environment of use according to claim 19, wherein when the dispenser is in operation in the environment of use, the means for absorbing thermal energy absorbs thermal energy and forms a dispensable composition, and means for forming a solution absorbs and imbibes fluid and forms a solution in the compartment.

32. The dispenser for delivering a beneficial agent composition to the biological environment of use according to claim 19, wherein when the dispenser is in operation in the environment of use, the means for absorbing thermal energy absorbs thermal energy and forms a dispensable composition, the means for forming a solution imbibes fluid and forms a solution in the compartment, and the dispensable composition and the solution form in situ a substantially immiscible interface therebetween.

33. The dispenser for delivering a beneficial agent composition to the biological environment of use according to claim 19, wherein the wall means that surrounds and defines the internal compartment comprises a member selected from the group consisting of an olefin polymer, a condensation polymer, a silicon polymer, and a carbohydrate polymer, 34. The dispenser for delivering a beneficial agent composition to the biological environment of use according to claim 19, wherein the means in the compartment for forming a solution is separated by a film from the means for absorbing thermal energy, which film lessens the incidence of a solution formed in situ mixing with the means for absorbing thermal energy.

35. A dispenser for delivering a beneficial agent formulation to an environment of use, the dispenser comprising;
   (a) a hollow body means for forming an internal lumen;
   (b) a heat-sensitive lipophilic formulation means in the lumen for absorbing heat from the environment of use for forming a deliverable formulation at a temperature of at least 31° C.;
   (c) a beneficial agent mixed with the heat-sensitve formulation means;
   (d) means in the lumen for forming a solution with aqueous fluid imbibed into the dispenser from the environment of use, said means forming an aqueous solution for exerting pressure against the heat-sensitive formulation means;
   (e) a wall that surrounds the hollow body means, the wall comprising in at least a part a composition that is permeable to the passage of fluid; and,
   (f) passageway means in the wall for connecting the exterior of the dispenser with the interior of the dispenser for delivering the beneficial agent to the environment of use at a controlled rate over a prolonged period of time.

36. A dispenser for delivering a beneficial agent formulation to an environment of use, the dispenser comprising;
   (a) a wall that surrounds and forms an internal compartment, the wall comprising at least in part a member selected from the group consisting of a cellulose ester, cellulose diester, cellulose triester, cellulose ether, cellulose ester-ether, cellulose acylate, cellulose diacylate, cellulose triacylate;
   (b) a thermo-responsive composition that forms a dispensable composition when contacted by thermal energy at a temperature up to 45° C. in the compartment, which composition is a carrier for a beneficial agent;
   (c) a beneficial agent blended with the carrier which produces a beneficial effect when administered by the dispenser to an animal;
   (d) an osmotically effective composition in the compartment that is substantially dry during storage temperature imbibes an aqueous fluid from the environment of use into the compartment and forms an aqueous solution at a temperature of from 30° C. to 45° C.; and,
   (e) means in the wall connecting the environment of use with the compartment for delivering the beneficial agent form the dispenser to the environment of use.

37. The dispenser for delivering a beneficial agent formulation to an environment of use according to claim 36, wherein the wall comprises a pore former.

38. A laminate useful for manufacturing a delivery device for dilivering a beneficial agent to a warm-blooded animal, wherein the laminate comprises (1) lamina means comprising at least in part a lipophilic member for containing a beneficial agent and for absorbing heat from the animal for forming a dispensable composition that is delivered from the delivery device to the aminal, and (2) lamina means for imbibing an aqueous fluid into the delivery device for forming an aqueous solution by mixing with fluid that enters the delivery device from the animal.

39. The laminate useful for manufacturing a delivery device for delivering a beneficial agent according to claim 38, wherein the (1) lamina means for forming a solution is an osmotically effective anhydrous solute, and the lamina for absorbing heat and the lamina for imbibing fluid are in contacting arrangement when the delivery device is in operation.

40. The lamina useful for manufacturing a delivery device for delivering a beneficial agent according to claim 38, wherein a (3) lamina means for decreasing the mixing of the (1) lamina means for absorbing heat with the (2) lamina means for forming a solution is positioned between lamina means (1) and lamina means (2).

* * * * *